United States Patent [19]

Barnes et al.

[11] 4,333,934
[45] Jun. 8, 1982

[54] IMIDAZOQUINOXALINES AND PYRROLOQUINOXALINES

[75] Inventors: Alan C. Barnes; David A. Rowlands, both of Cirencester, England

[73] Assignee: Roussel Uclaf, Paris, France

[21] Appl. No.: 118,445

[22] Filed: Feb. 4, 1980

[30] Foreign Application Priority Data

Feb. 9, 1979 [GB] United Kingdom ............... 7904648

[51] Int. Cl.³ ............... C07D 241/42; C07D 241/44; C07D 487/04
[52] U.S. Cl. ............... 424/250; 424/248.4; 424/258; 544/101; 544/344; 544/346; 546/84; 546/94
[58] Field of Search ............... 544/344, 346, 101; 546/84, 94; 424/248.4, 258, 250

[56] References Cited

U.S. PATENT DOCUMENTS

| | | | |
|---|---|---|---|
| 3,706,768 | 12/1972 | Bays | 260/335 |
| 4,075,343 | 2/1978 | Kadin et al. | 424/258 |
| 4,145,419 | 3/1979 | Rowlands et al. | 424/248.4 |
| 4,151,280 | 4/1979 | Rowlands et al. | 544/344 |
| 4,207,318 | 6/1980 | Rowlands et al. | 544/101 |
| 4,229,452 | 10/1980 | Warner et al. | 544/346 |

*Primary Examiner*—Paul M. Coughlan, Jr.
*Attorney, Agent, or Firm*—Hammond & Littell; Weissenberger and Muserlian

[57] ABSTRACT

Novel compounds of the formula

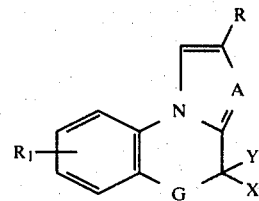

wherein A is selected from the group consisting of nitrogen and =CH—, G is selected from the group consisting of

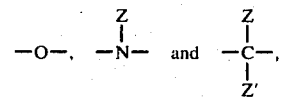

Z is selected from the group consisting of hydrogen and alkyl of 1 to 5 carbon atoms or taken with Y forms a carbon-nitrogen or carbon-carbon bond, Z' is selected from the group consisting of hydrogen and halogen, Y is hydrogen, or taken with Z is a carbon-nitrogen or carbon-carbon bond or taken with X is =O and X is hydrogen or taken with Y is =O, R is selected from the group consisting of hydroxymethyl, formyl, tetrazol-5-yl, N-(tetrazol-5-yl) carbamoyl, aminomethyl and carbamoyl, $R_1$ is selected from the group consisting of hydrogen, halogen and alkoxy of 1 to 5 carbon atoms and its non-toxic, pharmaceutically acceptable acid addition salts having antiallergic activity and their preparation.

18 Claims, No Drawings

IMIDAZOQUINOXALINES AND PYRROLOQUINOXALINES

STATE OF THE ART

Related compounds are described in U.S. Pat. Nos. 4,075,343, 4,145,419 and U.S. Pat. No. 4,151,280 and commonly assigned U.S. Patent applications Ser. No. 869,842 filed Jan. 16, 1978, U.S. Pat. No. 4,279,912, Ser. No. 958,561 filed Nov. 7, 1978 U.S. Pat. No. 4,208,318, and Ser. No. 61,626 filed July 30, 1979 U.S. Pat. No. 4,254,123.

OBJECTS OF THE INVENTION

It is an object of the invention to provide novel compounds of formula I and their non-toxic, pharmaceutically acceptable acid addition salts and their preparation.

It is another object of the invention to provide novel antiallergic compositions and to a novel method of treating allergic symptoms in warm-blooded animals.

These and other objects and advantages of the invention will become obvious from the following detailed description.

THE INVENTION

The novel compounds of the invention are selected from the group consisting of compounds of the formula

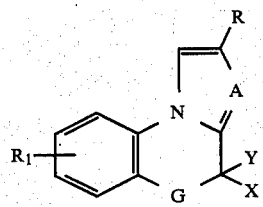

wherein A is selected from the group consisting of nitrogen and =CH—, G is selected from the group consisting of

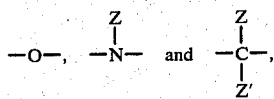

Z is selected from the group consisting of hydrogen and alkyl of 1 to 5 carbon atoms or taken with Y forms a carbon-nitrogen or carbon-carbon bond, Z' is selected from the group consisting of hydrogen and halogen, Y is hydrogen, or taken with Z is a carbon-nitrogen or carbon-carbon bond or taken with X is =O and X is hydrogen or taken with Y is =O, R is selected from the group consisting of hydroxymethyl, formyl, tetrazol-5-yl, N-(tetrazol-5-yl) carbamoyl, aminomethyl and carbamoyl, $R_1$ is selected from the group consisting of hydrogen, halogen and alkoxy of 1 to 5 carbon atoms and its non-toxic, pharmaceutically acceptable acid addition salts.

Examples of G when it is

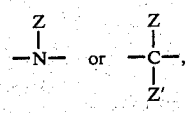

are those wherein Z is alkyl of 1 to 5 carbon atoms such as methyl, ethyl, propyl, isopropyl, n-butyl, isobutyl or pentyl and Z' may be hydrogen, chlorine or bromine. Examples of $R_1$ are hydrogen, chlorine, bromine, methoxy, ethoxy or isopropoxy.

Examples of suitable acids for the preparation of non-toxic, pharmaceutically acceptable acid addition salts are inorganic acids such as hydrochloric acid, hydrobromic acid, hydroiodic acid, nitric acid, sulfuric acid or phosphoric acid or organic acids such as acetic acid, formic acid, benzoic acid and other arylcarboxylic acids, maleic acid, fumaric acid, succinic acid, tartaric acid, oxalic acid, citric acid, glyoxylic acid, aspartic acid, alkane sulfonic acids such as methane sulfonic acid and ethane sulfonic acid and aryl sulfonic acids such as benzene sulfonic acid and p-toluene sulfonic acid.

Among the preferred compounds of formula I are those wherein R is hydroxy methyl, wherein R is formyl, wherein R is tetrazol-5-yl and those wherein $R_1$ is hydrogen and their non-toxic, pharmaceutically acceptable acid addition salts.

Among the specific preferred compounds of the invention are 2-(1H-tetrazol-5-yl)-imidazo-[1,2-a]-quinoxaline, 2-(1H-tetrazol-5-yl)-imidazo-[1,2-a]-quinoline, 8-methoxy-2-(1H-tetrazol-5-yl)-imidazo-[1,2-a]-quinoline, imidazo-[1,2-a]-quinoxaline-2-methanol, 5-ethyl-2-hydroxymethylimidazo-[1,2-a]-quinoxalin-4(5H)-one and 5-ethyl-2-hydroxymethylpyrrolo-[1,2-a]-quinoxalin-4(5H)-one and their non-toxic, pharmaceutically acceptable acid addition salts.

The process of the invention for the preparation of compounds of formula I wherein R is hydroxymethyl comprises reducing a compound of the formula

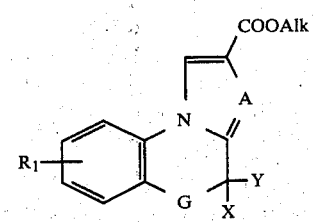

wherein A, G, Y, X and $R_1$ are hereinbefore defined and Alk represents an alkyl radical containing from 1 to 5 carbon atoms whereby the desired compound of formula I is obtained.

The reduction may be effected with a complex metal hydride such as lithium borohydride, preferably in an ether such as tetrahydrofuran as the solvent. The reduction is preferably effected at elevated temperatures, such as at reflux. When X and Y form =O, the reductions may be simultaneous or the reduction of the —COAlk group may be selectively effected.

The compounds of formula II may be prepared by the methods described in published French applications No. 2,387,230, No. 2,378,031 and No. 2,351,980. In known compounds wherein G is

and X and Y form a carbon-nitrogen bond, reduction with lithium borohydride gives the corresponding compound in which X and Y are both hydrogen.

The process of the compounds of formula I wherein R is formyl may be prepared by oxidizing a compound of formula I wherein R is hydroxymethyl. The oxidation may be effected with an oxidizing agent such as manganese dioxide or chromic oxide, preferably at elevated temperatures.

The process of the invention for the preparation of compounds of formula I wherein R is aminomethyl comprises catalytically hydrogenating a compound of the formula

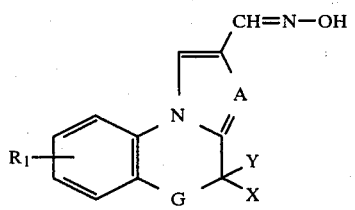

III wherein A, G, Y, X and $R_1$ are as hereinbefore defined. The catalytic hydrogenation is preferably effected with hydrogen in the presence of a metal catalyst such as palladium.

The process for the preparation of compounds of formula I wherein R is a tetrazol-5-yl comprises reacting a compound of the formula

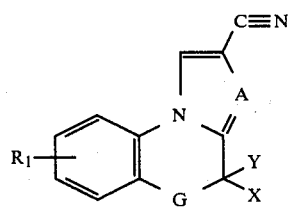

IV wherein A, G, Y, X and $R_1$ are as hereinbefore defined with sodium azide. The reaction is preferably effected at elevated temperatures in the presence of a weak acid such as ammonium chloride.

The process of the invention for the preparation of compounds of formula I wherein R is a N-(tetrazol-5-yl) carbamoyl comprises reacting a compound of the formula

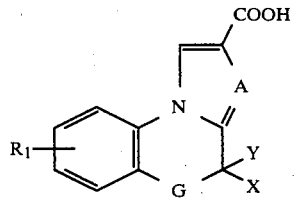

V wherein A, G, Y, X and $R_1$ are as hereinbefore defined or a reactive derivative thereof with 5-aminotetrazole. The reaction is preferably effected in the presence of a carbodimide reagent such as carbonyldiimidazole while using dimethyl formamide as solvent. Suitable reactive derivatives of the compound of formula V for use in the reaction include for example, the acid halides e.g. the acid chloride or bromide.

The preparation of compounds of formula I wherein R is a carbomoyl radical comprises reacting a compound of formula II as hereinbefore defined with ammonia.

The compounds of formula I may, if desired, be converted into their acid addition salts by reaction with an acid, for example, those set forth hereinbefore preferably in substantially equimolar quantities. If desired, the compounds of formula I prepared as described above may be converted directly to their acid addition salts without isolation.

The compounds of formula V may be prepared by hydrolysis of a compound of formula II, preferably under alkaline conditions e.g. using an alkali metal hydroxide.

The compounds of formula II wherein A is a nitrogen and G is

when they are not known, may for example be prepared by cyclization of a compound of the formula

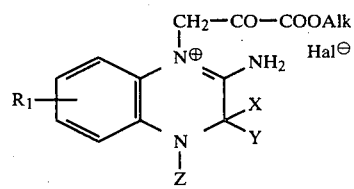

VI wherein $R_1$, Y, X, Z and Alk are as hereinbefore defined and Hal represents a chlorine or bromine atom, preferably by heating the reaction mixture at reflux. The compounds of formula VI may themselves be obtained, if desired, by reaction of a compound of the formula

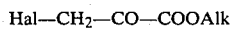

VII wherein Alk and Hal are hereinbefore defined with a compound of the formula

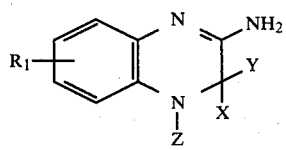

VIII wherein $R_1$, Y, X and Z are as hereinbefore defined, preferably in the presence of an organic solvent.

The compounds of formula VIII may be prepared by reacting the corresponding 2,3-dichloroquinoxaline with gaseous ammonia to replace one chlorine atom by $NH_2$, the reaction with ethanol giving, when Z is hydrogen, the desired lactam. The 2,3-dichloroquinoxaline may be prepared from the corresponding quinoxaline-2,3-diol by the method of Stevens et al. [JACS (1946) Vol. 68, p. 1035].

It will be appreciated that where $R_1$ is a halogen atom, the 2,3-dichloroquinoxaline is asymmetrical and conversion to a compound of formula VIII will give a mixture of isomers which may be separated at that stage, for example by chromatography, or may be reacted further as a mixture followed by separation of isomers at a later stage.

The compounds of formula IV may, for example, be obtained by reaction of a compound of formula III as hereinbefore defined with acetic anhydride.

Both the compounds of formula III and the compounds of formula IV are new compounds which, together with processes for their preparation and their use, constitute further features of the present invention. The compounds of formula III may be prepared, if desired, by reaction of a compound I as hereinbefore defined wherein R is formyl with hydroxylamine, preferably in the form of its hydrochloride. The reaction is preferably effected at elevated temperatures and preferably in the presence of sodium acetate.

The antiallergic compositions of the invention are comprised of an antiallergically effective amount of at least one compound of formula I and their non-toxic, pharmaceutically acceptable acid addition salts and an inert pharmaceutical carrier or excipient. The compositions may be in the form of tablets, coated tables, gelatin capsules, aerosols, granules, syrups, creams, ointments, suppositories and solutions and suspensions for injection.

The active ingredient may be incorporated in excipients customarily employed in pharmaceutical compositions such as for example, talc, gum arabic, lactose, starch, magnesium stearate, cacoa butter, aqueous or non-aqueous vehicles, fatty substances of animal or vegetable origin, paraffin derivatives, glycols, various wetting dispersing or emulsifying agents and/or preservatives.

Because of their antiallergic activity the compositions are useful in the treatment of asthma and bronchical asthma of allergic origins.

The novel method of the invention for relieving allergic symptoms in warm-blooded animals, including humans, comprises administering to warm-blooded animals an antiallergically effective amount of at least one compound of formula I and its non-toxic, pharmaceutically acceptable acid addition salts. The active compound may be administered orally, rectally, parenterally or topically. The usual daily dose is 0,005 to 1,5 mg/kg depending on the compound and the method of administration.

In the following examples there are described several preferred embodiments to illustrate the invention. However, it is to be understood that the invention is not intended to be limited to the specific embodiments.

EXAMPLE 1

4,5-dihydro-imidazo-[1,2-a]-quinoxaline-2-methanol

STEP A: 2-amino-1-carbethoxycarbonylmethyl-quinoxalinium bromide

A solution of 0.9 g of 2-amino-quinoxaline, 1.25 g of ethyl bromopyruvate and 25 ml of dimethoxyethane was stirred overnight at room temperature and was filtered to obtain 1.58 g of 2-amino-carbethoxycarbonylmethyl-quinoxalinium bromide in the form of a pale yellow crystalline solid.

STEP B: Ethyl imidazo-[1,2-a]-quinoxaline-2-carboxylate

A suspension of 0.4 g of the product of Step A in 15 ml of ethanol was refluxed for 2 hours and the resulting clear orange solution was concentrated to half its volume. The mixture was filtered to obtain 0.25 g of ethyl imidazo-[1,2-a]-quinoxaline-2-carboxylate as a pale yellow solid which were crystallized from an ether-methanol mixture to obtain the product in the form of soft-white needles melting at 184°–187° C. with decomposition.

Analysis: $C_{13}H_{11}N_3O_2$; molecular weight=241. Calculated: %C 64.72; %H 4.60; %N 17.42. Found: %C 64.80; %H 4.66; %N 17.47.

STEP C: 4,5-dihydro-imidazo-[1,2-a]-quinoxaline-2-methanol 2.8 g of lithium borohydride were added to a solution of 10 g of ethyl imidazo-[1,2-a]-quinoxaline-2-carboxylate of Step B in 230 ml of anhydrous tetrahydrofuran and the mixture was stirred at reflux for 18 hours. The resulting yellow suspension was poured into dilute hydrochloric acid to react with the boron complex and the mixture was made alkaline with sodium carbonate addition. The mixture was extracted with ethyl acetate and the organic phase was evaporated to dryness to obtain 5.9 g of 4,5-dihydro-imidazo-[1,2-a]-quinoxaline-2-methanol in the form of a buff crystaline solid melting at 172°–174° C. after crystallization from ethyl acetate to obtain a white crystalline solid.

IR Spectrum (KBr): NH=3300 cm$^{-1}$.

Analysis: $C_{11}H_{11}N_3O$; molecular weight=201. Calculated: %C 65.66; %N 5.51; %N 20.88. Found: %C 65.63; %N 5.54; %N 20.87.

EXAMPLE 2

Imidazo-[1,2-a]-quinoxaline-2-methanol and imidazo-[1,2-a]-quinoxaline-2-carboxaldehyde mixture A solution of 3 g of 4,5-dihydro-imidazo-[1,2-a]-quinoxaline-2-methanol in 500 ml of chloroform and 9 g of manganese dioxide was refluxed with stirring for 6 hours and the mixture was filtered hot and concentrated. The mixture was cooled and filtered to obtain 2.68 g of a imidazo-[1,2-a]quinoxaline-2-methanol and imidazo-[1,2-a]-quinoxaline-2-carboxaldehyde mixture and the latter was chromatographed over silica gel. Elution with a 97.5% chloroform-2.5% methanol mixture yielded first 0.23 g of imidazo-[1,2-a]-quinoxaline-2-carboxaldehyde and then 1.42 g of imidazo-[1,2-a]quinoxaline-2-methanol melting at 217°–220° C. Evaporation of the filtrate yielded 0.43 g of imidazo-[1,2-a]-quinoxaline-2-carboxaldehyde for a total yield of 0.66 g melting at 214°–215° C.

Imidazo-[1,2-a]-quinoxaline-2-carboxaldehyde

IR Spectrum (KBr):
CH=3130 cm$^{-1}$ (imidazole CH) and 2840 cm$^{-1}$ (aldehyde CH); CO=1700 cm$^{-1}$ (aldehyde carbonyl).

Analysis: $C_{11}H_7N_3O$; molecular weight=197. Calculated: %C 67.00; %H 3.85; %N 21.31. Found: %C 66.70; %H 3.63; %N 21.34.

Imidazo-[1,2-a]-quinoxaline-2-methanol

IR Spectrum (KBr):
OH=3200 cm$^{-1}$ (primary alcohol); CH=3110 cm$^{-1}$ (imidazol CH).

Analysis: $C_{11}H_9N_3O$; molecular weight=199. Calculated %C 66.32; %H 4.55; %N 21.09. Found: %C 66.25; %H 4.63; %N 21.09.

The yield of the aldehyde was increased by using 4 g of manganese dioxide per 1 g of dihydro-hydroxymethyl compound and refluxing the mixture overnight.

EXAMPLE 3

2-(1H-tetrazol-5-yl)-imidazo-[1,2-a]-quinoxaline

STEP A: Imidazo-[1,2-a]-quinoxaline-2-carboxaldehyde oxime

A solution of 1.4 g of hydroxylamine hydrochloride, 1.9 g of sodium acetate and 5 ml of water was added to a suspension of 3.10 g of imidazo-[1,2-a]-quinoxaline-2-carboxaldehyde in 30 ml of ethanol and the mixture was stirred at 90° C. for 4 hours and was evaporated to dryness. The white crystalline residue was triturated with water and was filtered. The product was dried in vacuo over phosphorus pentoxide to obtain 2.83 g of imidazo-[1,2-a]-quinoxaline-2-carboxaldehyde oxime melting at 243°–245° C.

Analysis: $C_{11}H_8N_4O$; molecular weight = 212. Calculated; %C 62.26; %H 3.80; %N 26.40. Found: %C 62.13; %H 3,84; %N 26.41.

STEP B: Imidazo-[1,2-a]-quinoxaline-2-carbonitrile

A solution of 2 g of the product of Step A in 20 ml of acetic anhydride was refluxed for 3 hours and was then cooled and poured into a sodium carbonate solution. The mixture was filtered to obtain 1.8 g of a buff crystalline solid which was crystallized from a methanol-chloroform mixture to obtain imidazo-[1,2-a]-quinoxaline-2-carbonitrile in the form of a buff crystalline solid melting at 281°–285° C. with decomposition.

IR Spectrum (KBr):
CN = 2225 cm$^{-1}$ (stretch of CN).

Analysis: $C_{11}H_6N_4$; molecular weight = 194. Calculated: %C 68.04. %H 3.11; %N 28.85. Found: %C 67.64; %H 3.21; %N 28.59.

Step C: 2-(1H-tetrazol-5-yl)-imidazo-[1,2-a]-quinoxaline 0.4 g of ammonium chloride and 0.45 g of sodium azide were added to a solution of 1 g of the product of Step B in 50 ml of dimethylformamide and the mixture was stirred overnight at 100° C. to obtain a white suspension. The mixture was cooled and was poured into water. The mixture was filtered to obtain 0.65 g of a buff crystalline product which was crystallized from a dimethylformamide-water mixture to obtain 2-(1H-tetrazol-5-yl)-imidazo-[1,2-a]-quinoxaline in the form of buff crystals melting at 320°–322° C. with decomposition.

Analysis: $C_{11}H_7N_7$; molecular weight = 237. Calculated: %C 55.69; %H 2.98; %N 41.33. Found: %C 55.47; %H 3.24; %N 40.83.

EXAMPLE 4

N-(1H-tetrazol-5-yl)-imidazo-[1,2-a]-quinoxaline-2-carboxamide

STEP A: Imidazo-[1,2-a]-quinoxaline-2-carboxylic acid 10 ml of 1 N sodium hydroxide solution were added to a suspension of 0.63 g of ethyl imidazo-[1,2-a]-quinoxaline-2-carboxylate, 10 ml of ethanol and 30 ml of water and the mixture was refluxed for one hour. The ethanol was evaporated under reduced pressure from the resulting clear yellow solution and the aqueous phase was acidified with concentrated hydrochloric acid. The mixture was filtered to obtain 0.6 g of imidazo-[1,2-a]-quinoxaline-2-carboxylic acid in the form of a buff crystalline solid melting at 274°–275° C.

Analysis: $C_{11}H_7N_3O_2$; molecular weight = 213. Calculated: %C 61.97; %H 3.31; %N 19.71. Found: %C 61.82; %H 3.33; %N 19.71.

STEP B: N-(1H-tetrazol-5-yl)-imidazo-[1,2-a]-quinoxaline-2-carboxamide

A solution of 0.8 g of imidazo-[1,2-a]-quinoxaline-2-carboxylic acid, 0.7 g of carbonyldiimidazole and 40 ml of dimethylformamide was stirred at 90° C. for 30 minutes and 0.35 g of anhydrous 5-amino-tetrazole were added to the resulting clear orange solution. The mixture was stirred at 90° C. for one hour and was cooled in a refrigerator. The mixture was filtered and the recovered product was washed well with ethyl acetate and dried in vacuo to obtain 1.17 g of N-(1H-tetrazol-5-yl)-imidazo-[1,2-a]-quinoxaline-2-carboxamide which after crystallization from dimethylformamide was a white crystalline solid melting at 280°–281° C. with decomposition.

IR Spectrum (KBr):
NH = 3100 cm$^{-1}$ (amide NH); CH = 3170 cm$^{-1}$ (imidazol CH);
CO = 1680 cm$^{-1}$ (amide carbonyl).

Analysis: $C_{12}H_8N_8O$; molecular weight = 280. Calculated: %C 51.43; %H 2.88; %N 39.98. Found: %C 51.54 %H 2.54; %N 39.98.

EXAMPLE 5

Imidazo-[1,2-a]-quinoline-2-methanol

A solution of 7.2 g of ethyl imidazo-[1,2-a]-quinoxaline-2-carboxylate in 140 ml of anhydrous tetrahydrofuran and 1.0 g of lithium borohydride was refluxed with stirring for 20 hours and was then cooled to room temperature. 2 N hydrochloric acid was added dropwise to the mixture until effervescence ceased and the clear solution was stirred for one hour and made alkaline with saturated sodium bicarbonate solution. The mixture was concentrated under reduced pressure to evaporate the tetrahydrofuran and the mixture was poured into 500 ml of water. The mixture was cooled in an ice bath and filtered to obtain 4.9 g of imidazo-[1,2-a]-quinoxaline-2-methanol in the form of a colorless solid. The filtrate was extracted with chloroform and the organic phase was dried over magnesium sulfate and evaporated to dryness to obtain an additional 0.60 g of the desired compound in the form of needles melting at 158°–159° C. after crystallization from an ether-ethyl acetate mixture.

IR Spectrum (KBr disc); λmax at 3300–2600 (OH); 1614, 1549, 1452, 1418, 1343, 1041, 1034, 998 and 802 cm$^{-1}$.

Analysis: $C_{12}H_{10}N_2O$; molecular weight = 198. Calculated: %C 72.71; %H 5.08; %N 14.13. Found: %C 72.70; %H 5.16; %N 14.13.

EXAMPLE 6

Imidazo-[1,2-a]-quinoline-2-carboxaldehyde

A mixture of 4.2 g of imidazo-[1,2-a]-quinoline-2-methanol, 16.0 g of manganese dioxide and 11 ml of chloroform was refluxed for 4 hours and was then cooled overnight. The mixture was filtered through cellulose powder and the filter was washed with chloroform. The filtrate was evaporated to dryness under reduced pressure and the residue was triturated with diethyl ether to obtain 3.4 g of imidazo-[1,2-a]-quinoline-2-carboxaldehyde in the form of needles melting at 184°–185° C. after crystallization from an ether-chloroform mixture.

IR Spectrum (KBr disc) max: 2805 (CHO), 1700 (C0), 1620, 1453, 1423, 1219, 1196, 811 and 753 cm$^{-1}$ Analysis: $C_{11}H_8N_2O$; molecular weight = 196. Calculated: %C 73.46; %H 4.11; %N 14.28. Found: %C 73.26; %H 4.20; %N 14.28.

EXAMPLE 7

2-(1H-tetrazol-5-yl)-imidazo-[1,2-a]-quinoline

STEP A: Imidazo-[1,2-a]-quinoline-2-carboxaldehyde oxime

A solution of 1.0 g of hydroxylamine hydrochloride, 1.35 g of sodium acetate and 20 ml of water was added to 2.40 g of imidazo-[1,2-a]-quinoline-2-carboxaldehyde in 60 ml of ethanol and the solution was refluxed with stirring for 2 hours and was concentrated under reduced pressure. 50 ml of water were added to the mixture with stirring and the mixture was filtered. The recovered product was washed with water and dried in vacuo over phosphorus pentoxide to obtain 2.55 g of a mixture of the syn and anti isomers of imidazo-[1,2-a]-quinoline-2-carboxaldehyde oxime. After crystallization from a chloroform-methanol mixture, the product melted at 224°–226° C.

IR Spectrum (KBr DISC) max: 3180 (OH); 1610, 1539, 1468, 1451, 1413, 1341, 1331, 1293, 1182, 918 and 880 cm$^{-1}$.

Analysis: $C_{12}H_9N_3O$; molecular weight=211. Calculated: %C 68.24; %H 4.29; %N 19.89. Found: %C 67.94; %H 4.41; %N 19.85.

STEP B: Imidazo-[1,2-a]-quinoline-2-carbonitrile

A mixture of 2.0 g of the product of Step A in 20 ml of acetic anhydride was stirred at reflux for 3 hours and was cooled to room temperature overnight. The mixture was poured into a saturated sodium carbonate solution and the resulting mixture was extracted with chloroform. The organic phase was washed with sodium carbonate solution and with water, dried over magnesium sulfate and evaporated to dryness under reduced pressure. The residue was triturated with ether and was filtered to obtain 1.3 g of imidazo-[1,2-a]-quinoline-2-carbonitrile in the form of pale yellow crystals melting at 244°–246° C. after crystallization from a chloroform-ether mixture.

IR Spectrum (KBr Disc) max: 2209 (CN); 1616, 1563, 1448, 1412, 1278, 1218, 1206, 1199 and 1139 cm$^{-1}$.

Analysis: $C_{12}H_7N_3$; Molecular weight=193. Calculated: %C 74.60; %H 3.65; %N 21.75. Found: %C 74.50; %H 3.79; %N 21.73.

STEP C: 2-(1H-tetrazol-5-yl)-imidazo-[1,2-a]-quinoline 0.40 g of ammonium chloride and 0.45 g of sodium azide were added with stirring at 40° C. to a solution of 1.0 g of the product of Step B in 50 ml of dimethylformamide and the mixture was stirred under nitrogen at 100° C. for 16 hours after which 0.20 g of ammonium chloride and 0.225 g of sodium azide were added. The mixture was stirred at 120° C. for 6 hours and after the addition of another 0.20 g of ammonium chloride and 0.225 g of sodium azide, the mixture was stirred at 100° C. for 16 hours and was then cooled to room temperature. 50 ml of water were added thereto dropwise and the mixture was filtered. The recovered product was washed with water, dried under vacuum over phosphorus pentoxide and was crystallized from a chloroform-methanol mixture to obtain 0.92 g of 2-(1H-tetrazol-5-yl)-imidazo-[1,2-a]-quinoline in the form of colorless crystals melting at 300°–300.5° C.

IR Spectrum (KBr disc) max: 3150–2400, 1631, 1618, 1541, 1510, 1450, 1341, 1204, 1078, 1066 and 950 cm$^{-1}$.

Analysis: $C_{12}H_8N_6$; molecular weight=236. Calculated: %C 61.01; %H 3.41; %N 35.58. Found: %C 60.86; %H 3.52; %N 35.85.

EXAMPLE 8

Imidazo-[1,2-a]-quinoline-2-methanamine dihydrochloride

A solution of 1.0 g of imidazo-[1,2-a]-quinoline-2-carboxaldehyde oxide in 100 ml of 0.25 N methanolic hydrogen chloride in the presence of 0.100 g of 10% palladized carbon was hydrogenated at atmosphere pressure for 4 hours and after 175 ml of hydrogen were absorbed, 0.200 g of additional catalyst were added thereto. The mixture was hydrogenated further at 50° C. under atmosphere pressure for 2 hours during which 62 ml of hydrogen were absorbed. The mixture was filtered through cellulose powder and the filtrate was concentrated under reduced pressure. Anhydrous ether was added to the concentrate which was then cooled in ice to induce crystallization. The mixture was filtered and the recovered product was dried at 50° C. under vacuo and was crystallization from a methanol-ether mixture to obtain 0.85 g of imidazo-[1,2-a]-quinoline-2-methanamine dihydrochloride in the form of hygroscopic colorless crystals melting at 320°–325° C. with decomposition.

IR Spectrum (KBr disc) max: 3540, 3380, 3100–2300, 1641, 1618, 1560, 1487, 1427, 1368, 1210, 1138 and 1173 cm$^{-1}$.

Analysis: $C_{12}H_{13}N_3Cl_2.0.5\ H_2O$; molecular weight=279. Calculated: %C 51.63; %H 5.05; %N 15.05; %Cl 25.40. Found: %C 51.84; %H 4.99; %N 15.37; %Cl 25.20.

EXAMPLES 9 to 11

The procedures of Examples 5,6 and 7, respectively, were repeated using as the starting material in Example 9, ethyl 5,8-dichloro-imidazo-[1,2-a]-quinoline-2-carboxylate [prepared as in French published application No. 2,378,031] and the products and their properties are reported in Table I.

EXAMPLES 12 to 14

The procedures of Examples 5,6 and 7, respectively, were repeated using as the starting material of Example 12, ethyl 8-methoxy-imidazo-[1,2-a]-quinoline-2-carboxylate [prepared as in published French application No. 2,378,031] and the products and their properties are reported in Table I.

EXAMPLE 15

Using the procedure of Example 8, the final product of Example 14 was used as the starting material and the final product and its properties are reported in Table I.

TABLE 1

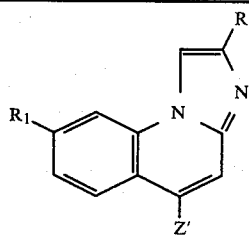

| Example no. | R | Z' | $R_1$ | Formula | mol | Calculated % C | % H | % N | % Cl | Found % C | % H | % N | % Cl |
|---|---|---|---|---|---|---|---|---|---|---|---|---|---|
| 9 | $CH_2OH$ | Cl | Cl | $C_{12}H_8N_2OCl_2$ | 267 | 53.96 | 3.02 | 10.49 | 26.55 | 54.09 | 3.08 | 10.45 | 26.40 |
| 10 | CHO | Cl | Cl | $C_{12}H_6N_2OCl_2$ | 265 | 54.37 | 2.28 | 10.57 | 26.57 | 54.15 | 2.41 | 10.44 | 26.46 |
| 11 Step A | CHNOH | Cl | Cl | $C_{12}H_7N_3OCl_2$ | 280 | 51.45 | 2.52 | 15.00 | 25.31 | 51.76 | 2.71 | 14.89 | 25.47 |
| 11 Step B | CN | Cl | Cl | $C_{12}H_5N_3Cl_2$ | 262 | 54.99 | 1.92 | 16.03 | 27.05 | 54.81 | 2.02 | 15.99 | — |
| 11 Step C | HN–N / N=N (tetrazole) | Cl | Cl | $C_{12}H_6N_6Cl_2$ | 304 | | | | | | | | * |
| 12 | $CH_2OH$ | H | $OCH_3$ | $C_{13}H_{12}N_2O_2$ | 228 | 63.41 | 5.30 | 12.27 | — | 68.37 | 5.34 | 12.23 | — |
| 13 | CHO | H | $OCH_3$ | $C_{13}H_{10}N_2O_2$ | 226 | 69.02 | 4.46 | 12.38 | — | 68.87 | 4.48 | 12.16 | — |
| 14 Step A | CHNOH | H | $OCH_3$ | $C_{13}N_{11}N_3O_2$ | 241 | 64.72 | 4.60 | 17.42 | — | 64.38 | 4.81 | 17.18 | — |
| 14 Step B | CN | H | $OCH_3$ | $C_{13}H_9N_3O$ | 223 | 69.95 | 4.06 | 18.82 | — | 69.97 | 4.15 | 18.96 | — |
| 14 Step C | HN–N / N=N (tetrazole) | H | $OCH_3$ | $C_{13}H_{10}N_6O$ | 266 | 58.64 | 3.79 | 31.56 | — | 58.37 | 3.93 | 31.32 | — |
| 15 | $CH_2NH_2$ | H | $OCH_3$ | $C_{13}H_{13}N_3O_2HCl \cdot 1\frac{1}{2}H_2O$ | 327 | 47.71 | 5.54 | 12.84 | 21.67 | 47.40 | 5.55 | 12.98 | 21.56 |

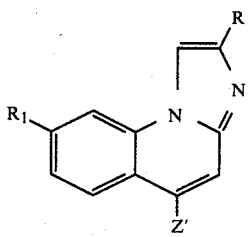

| Example no. | R | Z' | $R_1$ | M.P °C. | Recrystallisation solvent | Infra-red spectrum $cm^{-1}$ (KBr disc) |
|---|---|---|---|---|---|---|
| 9 | $CH_2OH$ | Cl | Cl | 207–10 | $EtOAc/Et_2O$ | 3320(OH), 1608, 1542, 1527, 1471w, 1440, 1396w, 1357, 1330, 1097, 1068, 1030, 993 |
| 10 | CHO | Cl | Cl | 280–5 | $CHCl_3/Et_2O$ | 3137(CH'), 2340(CHO), 1700(C=O), 1611, 1556, 1530, 1470, 1400, 1342, 1204, 1184, 1098, 1037, 1008 |
| 11 Stage A | CHNOH | Cl | Cl | 244–6 | $CHCl_3/Et_2O$ | 3500–2700(OH's), 1645w(C=N), 1609s, 1535, 1440, 1390w, 1354, 1327, 1277, 1190, 1179, 1098s, 1020 |
| 11 Stage B | CN | Cl | Cl | 286–8 | $CHCl_3$ | 3130(CH'), 2211(C≡N), 1608, 1551, 1528, 1431, 1342, 1325, 1300, 1183, 1094, 950 |
| 11 Stage C | HN–N / N=N (tetrazole) | Cl | Cl | 322–4 | — | 3140–2300, 1609, 1529, 1435, 1268, 1161, 1097, 1082, 1073, 1022, 951, 942 |
| 12 | $CH_2OH$ | H | $OCH_3$ | 173–5 | $EtOAc/Et_2O$ | 3105br(OH), 1630, 1550, 1490, 1441, 1408, 1372, 1347, 1286, 1246, 1170, 1150, 1036, 1013, 997 |
| 13 | CHO | H | $OCH_3$ | 190–3 | $CHCl_3/Et_2O$ | 3100, 2840(CHO), 1697, 1683, 1618, 1550, 1491, 1450, 1381, 1358, 1330, 1242, 1219, 1180, 1152, 1030, 992 |
| 14 Stage A | CHNOH | H | $OCH_3$ | 202–6 | $CHCl_3/Et_2O$ | 3450(OH), 1627s, 1614, 1548, 1377, 1331, 1292, 1240s, 1218, 1187, 1132 |
| 14 Stage B | CN | H | $OCH_3$ | 212–4 | $CHCl_3/Et_2O$ | 3150(CH'), 2220(C≡N), 1631, 1618, 1549, 1484, 1331, 1308, 1241, 1220, 1177, 1155, 1028 |
| 14 Stage C | HN–N / N=N (tetrazole) | H | $OCH_3$ | 305–6 | $(CH_3)_2S=O$ | 3000–2300, 1630, 1618, 1548, 1540, 1490, 1367, 1340, 1239, 1223, 1149, 1072, 1017, 951, 823 |
| 15 | $CH_2NH_2$ | H | $OCH_3$ | HCl salt | $CH_3OH/Et_2O$ | 3600–2400, 1650, 1624, 1612, 1503, 1480, 1384, 1248, 1228, 1106, 1019, 839 |

TABLE 1-continued 274-7

*Sample extremely insoluble in all solvents prohibiting satisfactory recrystallisation. High resolution mass spectrum showed M+ = 304.0015 ± 5mmu. $C_{12}H_6N_6Cl_2$ requires M+ = 304.0031

EXAMPLE 16

N-(1H-tetrazol-5-yl)-imidazo-[1,2-a]-quinoline-2-carboxamide 0.85 g (4 mmol) of imidazo-[1,2-a]-quinoline-2-carboxylic acid [prepared as in published French application No. 2,378,301] was heated at 160° C. in vacuo for one hour to remove water of crystallization and was then dissolved in 25 ml of dimethylformamide. The solution was stirred at 90° to 100° C. with 0.72 g (4.4 mmol) of carbonyldiimidazole and the mixture was stirred at 100° C. for 40 minutes to obtain a slight suspension. 0.375 g of anhydrous 5-amino-tetrazole were added to the mixture which was then stirred at 100° C. for 45 minutes and was then cooled to room temperature. 20 ml of ethyl acetate were added to the mixture and the mixture was cooled in ice and was filtered to obtain 1.12 g of N-(1H-tetrazol-5-yl)-imidazo-[1,2-a]-quinoline-2-carboxamide in the form of colorless crystals melting at 266°-268° C. after crystallization from dimethylformamide.

IR Spectrum (KBr disc): 3410 (NH), 3110, 1677 (C=O), 1586, 1397, 1252, 993 and 880 $cm^{-1}$.

Analysis: $C_{13}H_9N_7O$; molecular weight=279. Calculated: %C 55.91; %H 3.25; %N 35.11. Found: %C 55.74; %H 3.40; %N 34.91.

EXAMPLE 17

Using the procedure of Example 16, 8-methoxy-imidazo-[1,2-a]-quinoline-2-carboxylic acid was reacted to obtain 8-methoxy-N-(1H-tetrazol-5-yl)-imidazo-[1,2-a]-quinoline-2-carboxamide melting at 298°-301° C. after crystallization from dimethylformamide.

IR Spectrum (KBr disc): 3490 (NH), 3110, 1693, 1635, 1622, 1599, 1551 and 1241 $cm^{-1}$.

Analysis: $C_{14}H_{11}N_7O_2.0.5\ H_2O$; molecular weight=318. Calculated: %C 52.83; %H 3.80; %N 30.80. Found: %C 53.19; %H 3.82; %N 31.12.

EXAMPLE 18

Imidazo-[1,2-a]-quinoline-2-carboxamide 2.0 g of ethyl imidazo-[1,2-a]-quinoline-2-carboxylate were added to a solution of 0.100 g of sodium in 500 ml of ethanol and a slow stream of ammonia was bubbled therethrough with stirring for 30 minutes. The mixture stood under ammonia at room temperature for one week and was filtered to obtain 0.60 g of imidazo-[1,2-a]-quinoline-2-carboxamide in the form of colorless plates melting at 270°-271° C. The filtrate was concentrated under reduced pressure to 50 ml and 700 ml of water were added thereto. The mixture was filtered to recover an additional 0.50 g of the desired product. The first crop was analystically pure and the second crop was crystallized from a chloroform-methanol-ether mixture to obtain a melting point of 270°-271° C.

IR Spectrum(KBr disc): 3360 ($NH_2$), 3302 ($NH_2$) 1662 (C=O), 1616, 1580, 1540, 1391, 1358, 1335, 1318, 1278 and 1200 $cm^{-1}$.

Analysis: $C_{12}H_9N_3O$; molecular weight=211. Calculated: %C 68.24; %H 4.29; %N 19.89. Found: %C 68.00; %H 4.33; %N 19.87.

EXAMPLE 19

8-methoxy-imidazo-[1,2-a]-quinoxaline-2-carboxamide

Using the procedure of Example 18, ethyl 8-methoxy-imidazo-[1,2-a]-quinoline-2-carboxylate was reacted to obtain 8-methoxy-imidazo-[1,2-a]-quinoline-2-carboxamide melting at 273°-276° C.

IR Spectrum (KBr disc): 3260, 3150, 1700, 1672, 1630, 1616, 1570, 1540, 1391, 1338, 1278 and 1237 $cm^{-1}$.

Analysis: $C_{13}H_{11}N_3O_2$; molecular weight=241. Calculated: %C 64.72; %H 4.60; %N 17.42. Found: %C 64.62; %H 4.60; %N 17.38.

EXAMPLE 20

4,5-dihydro-5-ethyl-imidazo-[1,2-a]-quinoxaline-2-methanol

STEP A: 2-amino-1-carbethoxycarbonylmethyl-3-chloro-quinoxalinium bromide

A solution of 9 g of 2-amino-3-chloro-quinoxaline [prepared by heating under pressure 2,3-dichloro-quinoxaline and ammonia in ethanol by method of Saikachi et al (Chem. Pharm. Bull. Tokyo (1961), Vol. 9, p. 941], 12 g of ethyl bromopyruvate and 180 ml of dimethoxy ethane was stirred overnight and was filtered to obtain 5.33 of 2-amino-1-carbethoxycarbonylmethyl-3-chloro-quinoxalinium bromide in the form of a pale yellow crystalline solid. The filtrate was held in a refrigerator for 2 days to obtain 2 more crops of 1.20 and 3.62 g of product for a total yield of 10.22 g.

STEP B: Ethyl 4,5-dihydro-4-oxo-imidazo-[1,2-a]-quinoxaline-2-carboxylate

A suspension of 5 g of the product of Step A in 500 ml of ethanol was refluxed with stirring for 2 hours and the resulting clear yellow solution was concentrated and cooled in a refrigerator. The mixture was filtered to obtain 3.70 g of ethyl 4,5-dihydro-4-oxo-imidazo-[1,2-a]-quinoxaline-2-carboxylate in the form of a white crystalline solid which was crystallized from ethanol to obtain shiny white crystals melting at 292-293° C.

STEP C: Ethyl 4,5-dihydro-5-ethyl-4-oxo-imidazo-[1,2-a]-quinoxaline-2-carboxylate 0.1 g of sodium hydride as an 80% oil dispersion was added to a solution of 0.7 g of the product of Step B in 30 ml of dimethylformamide and the resulting solution was stirred for 10 minutes to form a gelatinous precipitate of a sodium salt. 0.6 g of ethyl iodide was added thereto and the mixture was stirred for 3 hours to obtain a clear yellow solution which was poured over ice. The mixture was filtered to obtain a 63% yield of ethyl 4,5-dihydro-5-ethyl-4-oxo-imidazo-[1,2-a]-quinoxaline-2-carboxylate in the form of a soft white solid which was crystallized from ethanol to obtain white shiny needles melting at 216-218° C.

Analysis: $C_{15}H_{15}N_3O_3$; molecular weight=285. Calculated: %C 63.d15; %H 5.30; %N 14.73. Found: %C 63.06; %H 5.26; %N 14.78. STEP D: 4,5-dihydro-5-ethyl-imidazo-[1,2-a]-quinoxaline-2-methanol A mixture of 3.13 g of ethyl 4,5-dihydro-5-ethyl-4-oxo-imidazo-[1,2-α]-quinoxaline-2-carboxylate, 0.5 g of lithium borohydride and 80 ml of anhydrous tetrahydrofuran was refluxed with stirring for 20 hours and the resulting suspension was poured into dilute hydrochloric acid. The mixture was stirred for 10 minutes to break the boron complex and the pale yellow clear solution was made alkaline with sodium carbonate addition. The mixture was extracted with ethyl acetate and the organic phase was evaporated to dryness to obtain 1.93 g of 4,5-dihydro-5-ethyl-imidazo-[1,2-a]-quinoxaline-2-methanol in the form of a buff crystalline solid which was crystallized from ethanol to obtain shiny white plates melting at 160°-165° C. with decomposition.

Analysis: $C_{13}H_{15}N_3O$; molecular weight=229. Calculated: %C 68.10; %N 6.59; %N 18.33. Found: %C 67.85; %N 6.63; %N 18.27.

EXAMPLE 21

5-ethyl-2-hydroxymethyl-imidazo-[1,2-a]-quinoxaline-4-(5H)-one 0.65 g of lithium borohydride were added to a solution of 4 g of ethyl 4,5-dihydro-5-ethyl-4-oxo-imidazo-[1,2-a]-quinoxaline-2-carboxylation in 105 ml of anhydrous tetrahydrofuran and the mixture was stirred overnight just below reflux and was then poured into dilute hydrochloric acid. The resulting clear solution was stirred for a few minutes and was then made alkaline with sodium carbonate addition. The resulting solution was extracted with ethyl acetate and the organic phase was evaporated to dryness to obtain 2.6 g of an orange-red solid. The said residue was triturated with ethanol and filtered to obtain 0.9 g of 5-ethyl-2-hydroxymethyl-imidazo-[1,2-a]-quinoxaline-4-(5H)-one in the form of a buff crystalline solid. The ethanol filtrate contained mainly 4,5-dihydro-imidazo-[1,2-a]-quinoxline.

The aqueous phase from the extraction stood for 2 days and was filtered to obtain an additional 0.55 g of the desired product for a total yield of 1.45 g. The combined yields were crystallized from ethanol to obtain a white crystalline solid melting at 215°-218° C.

IR Spectrum (KBr disc): OH=3400 cm$^{-1}$ ($CH_2OH$); CH=3110 cm$^{-1}$ (imidazole CH); CO=1655 (amide carbonyl).

Analysis: $C_{13}H_{13}N_3O_2$; molecular weight=243. Calculated: %C 64.19; %H 5.39; %N 17.27. Found: %C 64.12; %H 5.49; %N 17.26.

EXAMPLE 22

4,5-dihydro-5-ethyl-4-oxo-imidazo-[1,2-a]-quinoxaline-2-carboxaldehyde

A mixture of 3 g of manganese dioxide and a solution of 1.0 g of the product of Example 21 in 200 ml of chloroform was refluxed with stirring for one hour and the mixture was cooled and filtered through celite. The filtrate was evaporated to dryness to obtain 0.61 g of 4,5-dihydro-5-ethyl-4-oxo-imidazo-[1,2-a]-quinoxaline-2-carboxaldehyde in the form of a white crystalline solid which melted at 302°-306° C. after crystallization from an ethanol-chloroform mixture.

Analysis: $C_{13}H_{11}N_3O_2$; molecular weight=241. Calculated: %C 64.72; %H 4.60; %N 17.42. Found: %C 64.64; %N 4.82; %N 17.20.

EXAMPLE 23

5-ethyl-2-(1H-tetrazol-5-yl)-imidazo-[1,2-a]-quinoxaline-4(5H)-one

STEP A: 4,5-dihydro-5-ethyl-4-oxo-imidazo-[1,2-a]-quinoxaline-2-carboxaladehyde oxime A solution of 0.2 g of hydroxylamine hydrochloride and 0.25 g of sodium acetate in 2 ml of water was added to a suspension of 0.5 g of the product of Example 22 in 10 ml of ethanol and the mixture was stirred at 90° C. for 4 hours and was then filtered. The recovered product was washed with water and dried in vacuo to obtain 0.435 g of pure 4,5-dihydro-5-ethyl-4-oxo-imidazo-[1,2-a]-quinoxaline-2-carboxaldehyde oxime melting at 286°-288° C.

STEP B: 4,5-dihydro-5-ethyl-4-oxo-imidazo-[1,2-a]-quinoxaline-2-carbonitrile

A solution of 0.4 g of the product of Step A in 5 ml of acetic anhydride was refluxed for 2½ hours and was then cooled during which it solidified into a buff crystalline solid. The solid was triturated with aqueous sodium carbonate solution and was filtered. The product was washed with water and dried in vacuo to obtain 0.385 g of 4,5-dihydro-5-ethyl-4-oxo-imidazo-[1,2-a]-quinoxaline-2-carbonitrile in the form of a crystalline solid melting at >330° C.

IR Spectrum (KBr): CN=2225 cm$^{-1}$ (CN stretch).

STEP C: 5-ethyl-2-(1H-tetrazol-5-yl)-imidazo-[1,2-a]-quinoxaline-4(5H)-one

A solution of 0.325 g of the product of Step B, 0.11 g of ammonium chloride, 0.12 g of sodium azide and 15 ml of dimethylformamide was stirred at 100° C. overnight and was then cooled and poured into ice water. The mixture was filtered to obtain 0.29 g of 5-ethyl-2-(1H-tetrazol-5-yl)-imidazo-[1,2-a]-quinoxaline-4(5H)-one in the form of a buff crystalline solid which was crystallized from a chloroform-methanol mixture to obtain an off-white crystalline solid melting at 298°-300° C.

Analysis: $C_{13}H_{11}ON_7$; molecular weight=289. Calculated: %C 55.51; %H 3.94; %N 34.86. Found: %C 55.54; %H 3.96; %N 34.00

EXAMPLE 24

5-ethyl-2-hydroxymethyl-pyrrolo-[1,2-a]-quinoxaline-4(5H)-one

A suspension of 7.8 g (27.5 mmoles) of ethyl 4,5-dihydro-5-ethyl-4-oxopyrrolo-[1,2-a]-quinoxaline-2-carboxylate (prepared by the process of French Application No. 2,387,230), 3.5 g (160 mmole) of lithium borohydride and 500 ml of anhydrous tetrahydrofuran was stirred at room temperature for 12 hours and was then refluxed for 2 hours and was cooled. The tetrahydrofuran was evaporated to obtain a volume of 100 ml and dilute hydrochloric acid was added thereto. After gas evolution ceased, the mixture was neutralized with sodium bicarbonate and was extracted 3 times with ethyl acetate. The organic phase was dried and filtered and the filtrate was evaporated to dryness. The residue was triturated with a chloroform-ethyl acetate mixture to obtain 2 yields totalling 5.90 g of 5-ethyl-2-hydroxymethyl-pyrrolo-[1,2-a]-quinoxaline-4(5H)-one melting at 171°-173° C.

IR Spectrum: 1251, 1405, 1624, 3125 and 3420 cm$^{-1}$.

Analysis: $C_{14}H_{14}N_2O_2$; molecular weight=242. Calculated: %C 69.41; %H 5.82; %N 11.56. Found: %C 69.32; %H 5.89; %N 11.60.

EXAMPLE 25

4,5-dihydro-5-ethyl-4-oxopyrrolo-[1,2-a]-quinoxaline-2-carboxaldehyde

A mixture of 40 g of activated manganese dioxide and a solution of 5.0 g (20.6 mmole) of the product of Example 24 in 500 ml of chloroform was vigorously stirred for 3 hours and was then filtered through celite. The filtrate was evaporated to dryness and the residue was triturated with ether to obtain 3.9 g (80% yield) of 4,5-dihydro-5-ethyl-4-oxopyrrolo-[1,2-a]-quinoxaline-2-carboxaldehyde in the form of colorless needles melting at 252°-255° C.

IR Spectrum: 751, 1646, 1686 and 3115 cm$^{-1}$.

Analysis: $C_{14}H_{12}N_2O_2$; molecular weight=240. Calculated: %C 69.99; %H 5.03; %N 11.66. Found: %C 69.69; %H 5.13; %N 11.60.

EXAMPLE 26

5-ethyl-2-(1H-tetrazol-5-yl)-pyrrolo-[1,2-a]-quinoxaline-4(5H)-one

STEP A: 4,5-dihydro-5ethyl-4-oxopyrrolo-[1,2-a]-quinoxaline-2-carboxaldehyde oxime A mixture of 1.5 g (21.6 mmole) of hydroxylamine hydrochloride, 2 g (24.4 mmole) of sodium acetate, 3.4 g (14.1 mmole) of the product of Example 25, 20 ml of water and 40 ml of ethanol was warmed on a water bath for one hour and the mixture was evaporated to a volume of 20 ml. The mixture was filtered and the recovered product was rinsed with water and dried over $P_2O_5$ under vacuum to obtain 2.9 g of 4,5-dihydro-5-ethyl-4-oxopyrrolo-[1,2-a]-quinoxaline-2-carboxaldehyde oxime in the form of colorless needles melting at 262°-264° C.

IR Spectrum: 738, 1410, 1635 and 3220 cm$^{-1}$.

Analysis: $C_{14}H_{13}N_3O_2$; molecular weight=255. Calculated: %C 65.87; %H 5.13; %N 16.46. Found: %C 65.94; %H 5.27; %N 16.29.

STEP B: 4,5-dihydro-5-ethyl-4-oxopyrrolo-[1,2-a]-quinoxaline-2-carbonitrile

A mixture of 2.5 g (9.8 mmole) of the product of Step A in 40 ml of acetic acid anhydride was refluxed for 3 hours and was then poured into a mixture of water-sodium carbonate-ethyl acetate. The decanted organic phase was washed once with water, dried, filtered and evaporated to dryness. The residue was triturated with ether to obtain 1.8 g of 4,5-dihydro-5-ethyl-4-oxopyrrolo-[1,2-a]-quinoxaline-2-carbonitrile in the form of buff needles melting at 237°-239° C.

IR Spectrum: 745, 1413, 1655, 2220 and 3120 cm$^{-1}$.

Analysis: $C_{14}H_{11}N_3O_2$; molecular weight=239. Calculated: %C 70.87; %H 4.67; %N 17.71. Found: %C 70.83; %H 4.76; %N 17.85.

STEP C: 5-ethyl-2-(1H-tetrazol-5yl)-pyrrolo-[1,2-a]-quinoxaline-4(5H)-one 0.48 g (7.4 mmole) of sodium azide were added to a suspension of 1.3 g (5.5 mmole) of the product of Step B, 0.425 g (8.0 mmole) of ammonium chloride and 50 ml of dimethylformamide and the mixture was stirred at 130°-140° C. for 12 hours and was then cooled. 200 ml of water were added thereto and the mixture was filtered. The recovered product was drystallized from a methanol-ethyl acetate mixture to obtain 0.74 g (48% yield) of 5-ethyl-2-(1H-tetrazol-5yl)-pyrrolo-[1,2-a]-quinoxaline-4(5H)-one in the form of off-white crystals melting at 295°-297° C. with decomposition.

IR Spectrum: 740, 1389, 1440, 1591, 1630 and 3120 cm$^{-1}$.

Analysis: $C_{14}H_{12}N_6O$; molecular weight=280. Calculated: %C 59.99; %H 4.32; %N 29.98. Found: %C 59.39; %H 4.36; %N 29.63.

EXAMPLE 27

4,5-dihydro-5-ethyl-4-oxo-N-(1H-tetrazol-5yl)-pyrrolo-[1,2-a]-quinoxaline-2-carboxamide A mixture of 1.2 g (4.7 mmole) of 4,5-dihydro-5-ethyl-4-oxo-pyrrolo-[1,2-a]-quinoxaline-2-carboxylic acid (prepared by the process of French application No. 2,387,230), 0.81 g (5.0 mmole) of carbonyldiimidazole and 25 ml of anhydrous dimethylformamide was stirred until a clear solution was obtained and 0.425 g (5.0 mmole) of anhydrous 5-amino-tetrazole were added thereto. The mixture was stirred at room temperature for 30 minutes and was then filtered. The recovered product was washed with ethyl acetate and dried over $P_2O_5$ under vacuum to obtain 1.4 g of 4,5-dihydro-5-ethyl-4-oxo-N-(1H-tetrazol-5-yl)-pyrrolo-[1,2-a]-quinoxaline-2-carboxamide in the form of white crystals melting at 315°-318° C.

IR Spectrum: 747, 1276, 1599, 1672 and 3130 cm$^{-1}$.

Analysis: $C_{15}H_{13}N_7O_2$; molecular weight=331. Calculated: %C 55.72; %H 4.05; %N 30.33. Found: %C 55.57; %H 4.07; %N 30.42.

EXAMPLE 28

4H-imidazol-[2,1-c][1,4]-benzoxazine-2-methanol

A mixture of 23 g (0.1 mole) of methyl 4H-imidazo-[2,1-c][1,4]-benzoxazine-2-carboxylate (prepared by the process of French application No. 2,351,980) in 250 ml of anhydrous redistilled tetrahydrofuran was stirred at room temperature while adding 6 g (30% excess) of solid lithium borohydride thereto. The mixture heated up to 70° C. and was then stirred at room temperature for 5 hours. The mixture was poured into dilute hydrochloric acid and the pH of the mixture was adjusted to 1-2. The mixture was stirred until gas evolution ceased and was then neutralized with sodium bicarbonate. The solution was extracted 3 times with ethyl acetate and the combined organic phases were dried and filtered and the filtrate was reduced to a small volume. Ether was added thereto and the mixture was filtered. The recovered product was dried over $P_2O_5$ under vacuum to obtain 18.3 g of 4H-imidazo-[2,1-c][1,4]-benzoxazine-2-methanol in the form of colorless needles melting at 167°-168° C.

IR Spectrum (KBr): 736, 1238, 1445, 1541, 1606 and 3000-3300 cm$^{-1}$.

Analysis: $C_{11}H_{10}N_2O_2$: molecular weight=202. Calculated: %C 65.34; %H 4.98; %N 13.85. Found: %C 65.14; %H 5.11; %N 13.73.

EXAMPLE 29

4H-imidazol-[2,1-c][1,4]-benzoxazine-2-carboxaldehyde

A mixture of 4.9 g (24 mmole) of the product of Example 28, 30 g of activated manganese dioxide and 200 ml of chloroform was stirred at room temperature for 3 hours and was then filtered. The filter was washed with chloroform and the filtrate was evaporated to dryness. The residue was triturated with ether to obtain 3.9 g of 4H-imidazol-[2,1-c][1,4]-benzoxazine-2-carboxaldehyde in the form of colorless needles melting at 180°-182° C.

IR Spectrum (KBr): 755, 1039, 1509, 1698 and 1560 cm$^{-1}$.

Analysis: $C_{11}H_8N_2O_2$: molecular weight=200. Calculated: %C 66.00; %H 4.03; %N 13.99. Found: %C 65.74; %H 4.15; %N 13.91.

EXAMPLE 30

4H-2-(1H-tetrazol-5-yl)-imidazo-[2,1-c][1,4]-benzoxazine

STEP A: 4H-imidazo-[2,1-c][1,4]-benzoxazine-2-carboxaldehyde oxime

A solution of 0.80 g (11.5 mmole) of hydroxylamine hydrochloride and 1.1 g of (13.5 mmole) of sodium acetate in 20 ml of water was added to a suspension of 2.0 g (10 mmole) of the product of Example 29 in 50 ml of ethanol and the mixture was warmed on a water bath for 30 minutes until thin layer chromatography showed no aledhyde remaining. The mixture was cooled and was evaporated to a volume of 20 ml. The mixture was filtered and the recovered product was washed with a little water and dried over $P_2O_5$ under vacuum to obtain 2.05 g of 4H-imidazo-[2,1-c][1,4]-benzoxazine-2-carboxaldehyde oxime in the form of colorless needles softening at 210° C. and melting at 232°–233° C.

IR Spectrum (KBr): 747, 1250, 1518 and 2500–3300 $cm^{-1}$.

Analysis: $C_{11}H_9N_3O_2$: molecular weight=215. Calculated: %C 61.39; %H 4.22; %N 19.52. Found: %C 61.49; %H 4.32; %N 19.60.

STEP B: 4H-imidazo-[2,1-c][1,4]-benzoxazine-2-carbonitrile

A mixture of 1.90 g (8.8 mmole) of the product of Step A in 20 ml of acetic anhydride was refluxed for 3 hours and was then poured into a mixture of water-sodium carbonate-ethyl acetate. The decanted organic phase was washed with water, dried, and filtered and the filtrate was evaporated to dryness. The residue was triturated with ether and was filtered to obtain 1.45 g of 4H-imidazo-[2,1-c][1,4]-benzoxazine-2-carbonitrile in the form of buff crystalline needles melting at 226°–228° C.

IR Spectrum (KBr): 754, 1033, 1237, 1509, 1552, 2225 and 3120 $cm^{-1}$.

Analysis: $C_{11}H_7N_3O_2$: molecular weight=137. Calculated: %C 67.00; %H 3.58; %N 21.31. Found: %C 66.70; %H 3.69; %N 21.18.

STEP C: 4H-2-(1H-tetrazol-5-yl)-imidazo-[2,1-c][1,4]-benzoxazine

A mixture of 1.50 g of the product of Step B, 450 mg of sodium azide, 400 mg of ammonium chloride and 50 ml of dimethylformamide was stirred in an oil bath at 125° C. for 24 hours and the mixture was then cooled and diluted with 200 ml of water. The mixture was filtered and the recovered product was dried over $P_2O_5$ under vacuum and was crystallized from methanol containing activated charcoal to obtain 0.55 g of 4H-2-(1H-tetrazol-5-yl)-imidazo-[2,1-c][1,4]-benzoxazine in the form of off-white needles melting at 282°–285° C.

EXAMPLE 31

2-hydroxymethyl-5-ethyl-imidazo-[1,2-a]-quinoxaline-4(5H)-one hydrochloride 1.0 ml of concentrated hydrochloric acid was added to a suspension of 2.0 g of 2-hydroxymethyl-5-ethyl-imidazo-[1,2-a]-quinoxaline-4(5H)-one in 40 ml of hot methanol and the solution was filtered hot. The filtrate was extracted with 20 ml of ethyl acetate and the organic phase was cooled to 0° C. and filtered to obtain 2.0 g of 2-hydroxymethyl-5-ethyl-imidazo-[1,2-a]-quinoxaline-4(5H)-one hydrochloride in the form of colorless crystals melting at 224°–226° C.

IR Spectrum (KBr) OH=3260 $cm^{-1}$; CO=1678 $cm^{-1}$, 1579, 1547, 1380, 1370 and 1077 $cm^{-1}$.

Analysis: $C_{13}H_{13}N_3O_2.HCl$; molecular weight=279.5. Calculated: %C 55.81; %H 5.05; %N 15.02; %Cl 12.67. Found: %C 55.88; %H 5.11; %N 15.02; %Cl 12.64.

PREPARATION A

Ethyl pyrrolo-[1,2-a]-quinoxaline-2-carboxylate

A solution of 15 g of ethyl bromopyruvate in 75 ml of ethanol was added dropwise over 30 minutes to a refluxing solution of 9 g of quinaldine in 150 ml of ethanol and the mixture was refluxed for 90 minutes more and was cooled. The mixture was evaporated to dryness and the residue was dissolved in dilute hydrochloric acid. The solution was extracted with ethyl acetate and the organic phase was washed with water, with dilute sodium carbonate solution and then with water again, dried over magnesium sulfate and filtered. The filtrate was evaporated to dryness and the 300 g of reddish oil was chromatographed over silica gel. Elution with chloroform and the fractions were evaporated to dryness. The residue was crystallized from an ether-petroleum ether (b.p.=60°–80°C.) mixture to obtain 2.46 g of ethyl pyrrolo-[1,2-a]-quinoxaline-2-carboxylate in the form of pale lemon needles melting at 77°–78° C. Another 0.95 g of product was obtained from the mother liquors.

Analysis: Calculated: %C 75.30; %H 5.48; %N 5.85. Found: %C 75.29; %H 5.45; %N 5.85.

PREPARATION B

Pyrrolo-[1,2-a]-quinoxaline-2-carboxylic acid

A mixture of 1.2 g of the product of Preparation A, 50 ml of ethanol, 25 ml of water and 7.5 ml of 1 N sodium hydroxide solution was refluxed for 3 hours and was filtered hot. The filtrate was acidified with 9 ml of N hydrochloric acid and was then cooled in ice. The mixture was filtered and the recovered product was dried over $P_2O_5$ to obtain 870 mg of pyrrolo-[1,2-a]-quinoxaline-2-carboxylic acid melting at 242°–247° C. with decomposition.

Analysis: Calculated: %C 73.92; %H 4.29; %N 6.63. Found: %C 73.97; %H 4.33; %N 6.67.

EXAMPLE I

Tablets were prepared containing 5 mg of 2-(1H-tetrazol-5-yl)-imidazo-[1,2-a]-quinoxaline or 20 mg of 2-(1H-tetrazol-5-yl)-imidazo-[1,2-a]-quinoline or 25 mg of imidazo-[1,2-a]-quinoxaline-2-methanol and sufficient excipient of lactose, starch, talc and magnesium stearate to obtain a final tablet weight of 100 mg.

Aerosols were prepared whereby each dose consisted of 5 mg of 5-ethyl-2-hydroxymethyl-imidazo-[1,2-a]-quinoxaline-4(5H)-one hydrochloride, 0.15 mg of emulsifier and sufficient propellant for a total weight of 50 mg.

PHARMACOLOGICAL DATA

Passive cutaneous anaphylaxis (PCA) in rats

Cutaneous anaphylaxis was induced in groups of male rats weighing 180–220 g by intradermal (ID) sensitization with antiserum followed three days later by systemic challenge with antigen. Evans blue dye injected with the antigen was used as a marker to assess the severity of the local response. Anti-allergic drugs inhibit this reaction and this method is described by OVARY [(1962) in "Passive cutaneous Anaphylaxis in Allergology." 358–367 Ed. Brown: Pergamon Press:].

Preparation of Antigen for Sensitization (Alum precipitated ovalbumen)

1. Wash 120 grams Al (OH)$_3$ gel in 140 ml of saline (use of a macerater facilitates mixing).
2. Centrifuge at 3,000 r.p.m. for about 10 minutes.
3. Resuspend the precipitate with 300 ml of albumen egg powder (1.3 mg/ml) in saline and allow to stand for 30 minutes.
4. Centrifuge at 3,000 r.p.m. for 10 minutes.
5. Weigh the wet precipitate and to each gram weight, add 1 ml of saline. Store in refrigerator. (Quantity sufficient for 60 rats for a 3 day sensitization programme).

Preparation of Antiserm (i.e. anti-ovalbumen)

1. 1 ml of the alum precipitated ovalbumen was injected subcutaneously into 180–220 gram rats on days 0,2,4.
2. The rats were bled on day 14 either by cardiac puncture or via the dorsal abdominal aorta.
3. Equal quantities of serum from each animal were pooled and thoroughly mixed.
4. 2 ml aliquots were stored at $-20°$ C. in plastic tubes.

Serum Dilution for PCA

The antiserum for sensitization was diluted so that an ID injection of 0.1 ml into control animals gave an average score of a single spot of between 2.0–3.5 using a 5 point scoring system (0,1,2,3,4).

Method (A) SENSITIZATION:

Rats were anaesthetised with Nembutal (40–60 mg/kg i.p.) and were then sensitized by four ID injections (0.1 ml each) on shaved backs. The animals were then left for a period of three days to develop sensitization.

(B) CHALLENGE:

The sensitized rats were dosed orally or intravenously with the drug immediately prior to intravenous challenge via the superficial penile vein with 1 ml of an antigen/Evans blue mixture (1 mg albumen egg powder in 0.5 ml saline plus 0.5 ml of 1% Evans blue). The injections were speeded up by using an automatic 1 ml self-filling glass syringe. The "challenged" rats were killed after 30 minutes, (usually pithed) and their skin on the dorsal surface was removed. The degree and area of blueing, proportional to the anaphylactic reaction was assessed on a five point scoring system.

Calculations

1. Total scores for sites 1,2,3 and $4 = X$
2. Mean value of X for each group$= \overline{X}$
3. $\overline{X} t = \overline{X}$ for test group
   $\overline{X} c = \overline{X}$ for control group
4.

$$\% \text{ inhibition} = \frac{\overline{X}c - \overline{X}t}{\overline{X}c} \times \frac{100}{1}$$

5. ED$_{50}$=dose of drug giving 50% inhibition.

ED$_{50}$ values for compounds tested in the passive cutaneous anaphylaxis screen:

| COMPOUND OF EXAMPLE | ED$_{50}$ in mg/kg i.v. | p.o. |
|---|---|---|
| 2 (as hydrochloride) | 0.16 | 0.068 |
| 3 (as hydrochloride) | 0.14 | 0.084 |
| | 0.012 | 0.089 |
| 5 | — | 0.36 |
| 6 | — | 0.09 |
| 7 | 0.026 | 0.105 |
| 8 | 0.11 | 0.98 |
| 12 | 0.27 | 0.24 |
| 13 | 0.12 | 0.40 |
| 14 | 0.01 | 0.12 |
| 15 | 3.39 | — |
| 21 | | 0.062 |
| 22 | — | 0.077 |
| 24 | — | 0.045 |
| 26 | 0.011 | 0.439 |
| 30 | 0.33 | — |

Various modifications of the products and processes of the invention may be made without departing from the spirit or scope thereof and it is to be understood that the invention is to be limited only as defined in the appended claims.

We claim:

1. A compound selected from the group consisting of compounds of the formula

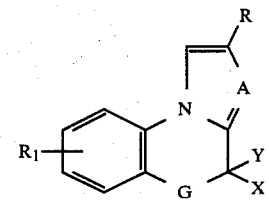

wherein A is selected from the group consisting of nitrogen and =CH—, G is

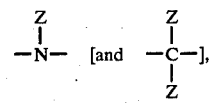

Z is selected from the group consisting of hydrogen and alkyl of 1 to 5 carbon atoms or taken with Y forms a carbon-nitrogen bond, Y is hydrogen, or taken with Z is a carbon-nitrogen bond or taken with X is =O and X is hydrogen or taken with Y is =O, R is selected from the group consisting of hydroxymethyl, formyl, N-(tetrazol-5-yl)-carbamoyl, aminomethyl and carbamoyl, R$_1$ is selected from the group consisting of hydrogen, halogen and alkoxy of 1 to 5 carbon atoms and its non-toxic, pharmaceutically acceptable acid addition salts.

2. A compound of claim 1 wherein R is selected from the group consisting of hydroxymethyl and formyl.

3. A compound of claim 1 wherein R is hydroxymethyl and R$_1$ is hydrogen.

4. A compound of claim 1 which is selected from the group consisting of imidazo-[1,2-a]-quinoxaline-2-methanol and its non-toxic, pharmaceutically acceptable acid addition salts.

5. A compound of claim 1 which is selected from the group consisting of 5-ethyl-2-hydroxymethylimidazo-

[1,2-a]-quinoxalin-4(5H)-one and its non-toxic, pharmaceutically acceptable acid addition salts.

6. A compound of claim 1 which is selected from the group consisting of 5-ethyl-2-hydroxymethylpyrrolo-[1,2-a]-quinoxalin-4(5H)-one and its non-toxic, pharmaceutically acceptable acid addition salts.

7. An antiallergic composition comprising an antiallergically effective amount of at least one compound of claim 1 and an inert pharmaceutical carrier.

8. A composition of claim 7 wherein R is selected from the group consisting of hydroxymethyl and formyl.

9. A composition of claim 7 wherein R is hydroxymethyl and $R_1$ is hydrogen.

10. A composition of claim 7 wherein the compound is selected from the group consisting of imidazo-[1,2-a]-quinoxaline-2-methanol and its non-toxic, pharmaceutically acceptable acid addition salts.

11. A composition of claim 7 wherein the compound is selected from the group consisting of 5-ethyl-2-hydroxymethylimidazo-[1,2-a]-quinoxalin-4(5H)-one and its non-toxic, pharmaceutically acceptable acid addition salts.

12. A composition of claim 7 wherein the compound is selected from the group consisting of 5-ethyl-2-hydroxymethylpyrrolo-[1,2-a]-quinoxalin-4(5H)-one and its non-toxic, pharmaceutically acceptable acid addition salts.

13. A method of relieving allergic symptoms in warm-blooded animals comprising administering to warm-blooded animals an antiallergically effective amount of at least one compound of claim 1.

14. A method of claim 13 wherein R is selected from the group consisting of hydroxymethyl and formyl.

15. A method of claim 13 wherein R is hydroxymethyl and $R_1$ is hydrogen.

16. A method of claim 13 wherein the compound is selected from the group consisting of imidazo-[1,2-a]-quinoxaline-2-methanol and its non-toxic, pharmaceutically acceptable acid addition salts.

17. A method of claim 13 wherein the compound is selected from the group consisting of 5-ethyl-2-hydroxymethylimidazo-[1,2-a]-quinoxalin-4(5H)-one and its non-toxic, pharmaceutically acceptable acid addition salts.

18. A method of claim 13 wherein the compound is selected from the group consisting of 5-ethyl-2-hydroxymethylpyrrolo-[1,2-a]-quinoxalin-4(5H)-one and its non-toxic, pharmaceutically acceptable acid addition salts.

* * * * *